United States Patent
Bell et al.

(12)

(10) Patent No.: US 6,365,176 B1
(45) Date of Patent: Apr. 2, 2002

(54) NUTRITIONAL SUPPLEMENT FOR PATIENTS WITH TYPE 2 DIABETES MELLITUS FOR LIPODYSTROPHY

(75) Inventors: Stacey J. Bell, Belmont; Judith Shabert, Brookline, both of MA (US)

(73) Assignee: Functional Foods, Inc., Belmont, MA (US)

( * ) Notice: Subject to any disclaimer, the term of this patent is extended or adjusted under 35 U.S.C. 154(b) by 0 days.

(21) Appl. No.: 09/664,227

(22) Filed: Sep. 18, 2000

Related U.S. Application Data

(63) Continuation-in-part of application No. 09/634,247, filed on Aug. 8, 2000.

(51) Int. Cl.[7] .............................................. A61K 47/00
(52) U.S. Cl. ...................... 424/439; 424/400; 424/442; 424/450; 424/451; 424/489
(58) Field of Search .................................. 424/400, 439, 424/464, 486; 514/52, 866, 904, 905, 960; 222/143

(56) References Cited

PUBLICATIONS

Shabert, J. and Ehrlich, N., *The Ultimate Nutrient Glutamine*, Avery Publishing Group, Garden City Park, New York (1994).

Kotler, D.P., "Update on Metabolic and Morphologic Abnormalities in HIV," Serono Symposia USA, Norwell, Massachusetts, 2000 (10 pages).

*Primary Examiner*—Thurman K. Page
*Assistant Examiner*—Charesse L. Evans
(74) *Attorney, Agent, or Firm*—Hamilton, Brook, Smith & Reynolds, P.C.

(57) ABSTRACT

Described herein is a nutritional supplement to be incorporated into the diet of a type 2 diabetic or an individual having lipodystrophy. The supplement provides active food-grade ingredients to improve the management of blood glucose and blood lipid levels. The supplement additionally aids in the improvement of the effects of platelet aggregation. The supplement should be taken daily during or at the end of the two largest meals, where most of the fat and cholesterol are likely to be ingested.

42 Claims, No Drawings

NUTRITIONAL SUPPLEMENT FOR PATIENTS WITH TYPE 2 DIABETES MELLITUS FOR LIPODYSTROPHY

RELATED APPLICATION

This application is a continuation-in-part of U.S. application Ser. No. 09/634,247 filed Aug. 8, 2000, the entire teachings of which are incorporated herein by reference.

BACKGROUND OF THE INVENTION

Type 2 diabetes mellitus affects 100 to 120 million people globally and 16 million nationally, about half of whom are unaware that they have the condition. Diabetes is a metabolic disorder defined by elevated blood glucose concentrations due to insulin dysfunction. The concomitant effects of the disease are defective insulin secretions, relative (rather than absolute) insulin deficiency, insulin resistance, and abnormal blood lipid levels. The specific etiologies of the type 2 diabetes are unknown, but autoimmune destruction of β-cells does not occur as seen in type 1 diabetes. Insulin levels may be normal or elevated, but the insulin itself is defective and unable to control blood glucose concentrations. The risk of developing microvascular complications from diabetes is related to hyperglycemia, and this increases with slight increases in hemoglobin $Al_c$ (Hgb $Al_c$) and with prolonged exposure to high glucose concentrations. Hyperglycemia is also implicated in causing macrovascular complications such as coronary artery disease, peripheral vascular disease, and stroke, but the relationship is less clear.

Postprandial hyperglycemia contributes substantially to overall glycemic control, and its role on the pathogenesis of the long-term microvascular and macrovascular complications of diabetes has generally been under-appreciated. Once diabetes is diagnosed, there is a progressive worsening of hyperglycemia in both the fasting and postprandial state. Since neither the oral agents (sulfonylureas) nor insulin can create the brief rise in insulin that normally accompanies a meal to mitigate this problem, the first line of therapy in type 2 diabetes is nutritional management, which as been recently referred to as "medical nutrition therapy" (MNT) (American Diabetes Association, *Diabetes Care*, 23(1):543–546 (2000)). This is integral to total diabetes management and is most effective if it involves an individualized plan devised by a registered dietitian or a nurse-dietitian team, and includes self-management training. Usually, the goals of MNT include maintenance of near-normal blood glucose levels by balancing food and blood glucose regulation medications (if prescribed), achievement of optimal serum lipid levels and blood pressure, provision of adequate calories for maintaining ideal weight, prevention and treatment of complications, and improvement in overall health.

Metabolic disorders such as hypertriglyceridemia, hypercholesterolemia and hyperglycemia are prevalent among HIV-infected individuals. Morphological changes accompany these metabolic disorders and have been referred to as lipodystrophy syndrome, although it is thought that there are two distinct syndromes. Affected individuals show fat redistribution, such as fat loss (e.g., in face) or fat accumulation (e.g., in abdominal area). These metabolic disorders may be attributed to high active antiretroviral therapy (HAART). Left untreated, the downstream adverse consequences of lipodystrophy include atherogenesis and atherosclerotic vascular disease. Thus, there is a need to provide nutritional supplementation to manage these metabolic disorders.

SUMMARY OF THE INVENTION

The invention relates to a nutritional supplement containing bioactive food-grade ingredients, which can help with the management of type 2 diabetes mellitus and metabolic disorders associated with lipodystrophy.

The nutritional supplement comprises a low glycemic index carbohydrate source, a source of protein, a source of fat, a source of sterol and/or stanol, a source of chromium, a source of salicylic acid, and a source of ginseng. In preferred embodiments, the nutritional supplement comprises, for a 45 kcal serving, from about 1 to about 25 grams carbohydrate (preferably as a combination of low glycemic index carbohydrates such as konjac, fructose, barley flakes, psyllium), from about 1 to about 10 grams protein, from about 1 to about 10 grams fat, from about 0.5 to about 4 grams plant sterol, from about 1 to about 2000 micrograms chromium (e.g., as chromium picolinate), from about 1 to about 325 milligrams salicylic acid (e.g., from a natural source like willow bark), and from about 1 mg to about 5 grams ginseng. The ranges used herein are based upon a single serving, where two servings are needed per day. Vitamins and minerals in amounts recommended daily to supplement the diet can also be optionally added.

The nutritional supplement can be made in a variety of forms, such as pharmaceutical compositions (e.g., tablet, powder, suspension, liquid, capsule, gel), nutritional beverages, puddings, confections (i.e., candy), ice cream, frozen confections and novelties, or non-baked, extruded food products such as bars. The preferred forms of the nutritional supplement are as a nutritional beverage and as a bar, such as a non-baked, extruded snack bar. In another embodiment, the ingredients of the nutritional supplement can be administered separately, such as by incorporating certain components (e.g., bitter tasting ones) into a capsule or tablet and the remaining ingredients are provided as a powder or nutritional bar. The supplement can be formulated for single or multiple daily administration, preferably twice daily, during or following the two meals in which the greatest amount of carbohydrate, cholesterol and fats are to be consumed.

The invention flier pertains to therapeutic methods for managing conditions associated with type 2 diabetes. In another embodiment, the nutritional supplement can be administered to HIV-infected individuals to prevent and/or treat metabolic disorders associated with lipodystrophy, such as insulin resistance, atherogenesis and cardivascular disease. The nutritional supplement can be administered to an individual to aid in the management of blood glucose levels and/or blood glucose levels. The risk of developing microvascular and macrovascular complications, such as atherogenesis and aterosclerotic vascular disease, associated with type 2 diabetes and lipodystrophy are lessened.

DETAILED DESCRIPTION OF THE INVENTION

The invention pertains to a nutritional supplement that provides nutritional support for people with type 2 diabetes mellitus. The invention further pertains to methods for effectively managing three aspects of type 2 diabetes [i.e., blood sugar (e.g., lowers postprandial and fasting blood glucose), blood lipids (e.g., total cholesterol fand LDL-cholesterol), and platelet aggregation] for a patient in need thereof. In another embodiment, the nutritional supplement can be administered to HIV-infected individuals to prevent and/or treat the metabolic changes associated with lipodystrophy, such as insulin resistance, atherogenesis and cardiovascular disease. Use of the nutritional supplement is not intended to take the place of the prescribed diet, exercise, and medication regimen, recommended for individuals having type 2 diabetes or lipodystrophy; rather it works as an adjunctive therapy in those patients who are compliant with their healthcare providers' suggestions.

The nutritional supplement can be made in a variety of forms such as a pharmaceutical composition (e.g., tablet, powder, suspension, liquid, capsule, gel), nutritional beverages, puddings, confections (i.e., candy), ice cream, frozen confections and novelties, or non-baked, extruded food products such as bars, to assist patients with the management of diabetes.

The nutritional supplement of the invention, suitable for individuals with type 2 diabetes mellitus or lipodystrophy, comprises a low glycemic index carbohydrate sources, a source of protein, a source of fat, a source of sterol and/or stanol, a source of chromium, a source of salicylic acid, and a source of ginseng. In particular, the nutritional supplement includes the following components: total carbohydrates, from about 1 to about 25 grams; protein, from about 1 to about 10 grams; fat, from about 1 to about 10 grams; plant sterol, from about 0.5 to about 4 grams; chromium, from about 1 to about 2,000 micrograms; willow bark or aspirin, from about 1 to about 325 milligrams; salicylic acid and ginseng, from about 1 mg to about 5 grams.

In a preferred embodiment, the nutritional supplement should approximately be comprised of (with about 20 to about 40 grams being preferred and 40 g being most preferred) about 10 g to about 15 g powder in 8 oz. water, from about 2 to about 10 grams of total carbohydrate, from about 1 to about 5 grams protein, from about 1 to about 5 grams fat, from about 0.5 to about 2 grams plant sterol, from about 50 to about 1000 micrograms chromium, from about 20 to about 80 milligrams salicylic acid source, and from about 100 to 200 milligrams ginseng.

In another embodiment, additional ingredients can be incorporated into the nutritional supplement for patients with lipodystrophy. In addition to the ingredients provided above, the nutritional supplement further comprises from about 1 to about 80 grams glutamine (with about 20 to about 40 grams being preferred; and 40 g being most preferred), from about 100 mg to about 20 grams N-acetyl cysteine (NAC; with about 1 to about 2 grams being preferred; and 1 gram being most preferred), from about 0.5 to about 25 grams of whey protein and from about 1 to about 2×RDI of antioxidants.

The nutritional supplement can be formulated into a snack to be taken as part of the diet or it can be formulated as a meal replacement. For a snack, the nutritional supplement should provide from about 1 to about 250 kcal per serving; from about 20 to about 100 kcal being preferred; and from about 45 to about 50 kcal being most preferred. As a meal replacement, the nutritional supplement will provide from about 300 kcal to about 350 kcal per serving.

For the purposes of this invention, a preferred nutritional supplement comprises the components described above as a single serving (serving unit), whereby one or a plurality (preferably, two) of these supplement(s) is(are) consumed daily. Preferably, two servings (e.g., 8 oz. water with 10–15 g powder) should make up 90 kcal and 1 bread exchange. In a preferred embodiment, each serving (serving size) contains 45 kcal and is comprised of macronutrient percentages in concert with the dietary recommendations of the American Diabetic Association. Other serving sizes are contemplated in the invention. The total amount of each ingredient should be appropriately adjusted. The supplement is most effective if taken during or after the midday and the evening meal, because after these, postprandial blood glucose levels are highest. The product contains active food compounds that help minimize hyperglycemia and hyperlipidemia. These conditions have been identified by the leaders in the field of diabetes as the major health risks associated with the condition. Fortunately, they can be effectively managed through food.

The use levels for ingredients incorporated into the nutritional supplement are illustrated in the chart below in relation to an about 10 to about 15g size serving of powder in 8 oz. water, and represents broadest, preferred and most preferred embodiments (all ingredients are qualified with the term "about").

| Nutrients (per serving) | Optimal | Preferred Range | Recommended Range |
|---|---|---|---|
| Carbohydrate | 7 g total<br>1 g konjac<br>2 g fructose<br>1 g barley<br>1 psyllium<br>2 g other (e.g. flavorings, colors) | 2–10 g total<br>0.5–5 g konjac<br>0.5–5 g fructose<br>0.5–5 g barley<br>0.5–5 g psyllium | 1–25 g total<br>0.5–11 g konjac<br>0.5–11 g fructose<br>0.5–11 g barley<br>0.5–11 g psyllium |
| Protein | 2 g | 1–5 g | 1–10 g |
| Fat | 1.5g | 1–5 g | 1–10 g |
| Plant Sterol | 0.8g | 0.5–2 g | 0.5–4 g |
| Chromium | 100 µg | 50–1,000 µg | 1–2,000 µg |
| Willow Bark (Salix alba) or Aspirin | Not to exceed 40 mg active compound (acetylsalicylic acid) or 267 mg willow bark (15% concentration of active compound) | 20–80 mg active compound | 1–325 mg active compound |
| Ginseng | 100 mg - Dose varies based on concentration of genosides | 100–200 mg | 1 mg to 5 g |
| Glutamine | 40 g | 20–40 g | 1–80 g |
| N-acetyl cysteine | 1 g | 1–2 g | 100 mg to 20 g |
| Whey protein (for lipodystropy embodiment) | 1.5g | 0.5–5g | 0.5–25 g |
| Antioxidants | 2 × RDI | 1–2 × RDI | 1–2 × RDI |

The ingredients that make up the nutritional supplement are further described in detail below and with regard to their relative role each contributes to therapeutic advantages of the invention.

Carbohydrates

Too much glucose released into the blood at once raises insulin and serotonin levels, which could decrease appetite or the desire for carbohydrate-rich foods at the next meal. Use of low-glycemic-index foods seems to be associated with better glucose control. Simple sugars usually cause a greater rise in blood glucose than starchy foods (Anderson, J. S. et al., *Modern Nutrition in Health and Disease*, pp.1259–86 (1994)). Bread and potatoes raise blood glucose more than beans. Other non-carbohydrate containing food ingested at the same time as carbohydrates (e.g., fat, fiber, protein) reduce postprandial blood glucose and insulin levels. The glycemic index is the area under the curve (AUC) in a plot of blood sugar measurements versus time, wherein the blood sugar measurements are taken over a period of time after a carbohydrate meal. Thus, the glycemic index of a carbohydrate is a relative measure of the rate and amount of glucose released into the blood from a carbohydrate.

In a preferred embodiment, the nutritional supplement contains one or more carbohydrates having a low glycemic index (e.g., from less than about 70). In a preferred embodiment the carbohydrate has a low glycemic index (e.g., konjac mannan, fructose, barley flakes (e.g., hulless)) and the carbohydrate provides a source of fiber (e.g., whey bran, cellulose, oat bran, guar, pectin, psyllium) comprising about 2 to about 10 g carbohydrate per serving, of which two are recommended per day.

Patients with type 2 diabetes consuming very high fiber diets (50 g versus the recommended 24 g) had significantly lower mean daily postprandial plasma glucose concentrations and mean daily urinary glucose excretions (Chandalia, M., N. Engl J. Med., (342): 1392–1398 (2000)). The overall decrease in plasma glucose was similar to that typically achieved with an oral hypoglycemic drug (Rendell, M., N. Engl. J. Med., (342): (2000)). Blood lipids (total cholesterol, triglycerides, and very-low density lipoprotein cholesterol concentrations) were also significantly lower than in the lower fiber group.

Psyllium husk fiber is a viscous, mostly water-soluble fiber prepared from blonde psyllium seed (Plantago ovata). Strong support exists from a meta-analysis showing that about 10 g of psyllium per day significantly lowers both total cholesterol (4%; p<0.0001) and low density lipoprotein (LDL) cholesterol (7%; p<0.0001) (Anderson J. W. et al., Am. J. Clin. Nutr., (71): 472–9 (2000)). This prompted the FDA to grant a "health claim" for the use of psyllium to reduce the risk of cardiovascular disease. Later, Anderson and colleagues observed similar effects of psyllium on the blood lipid levels of patients with primary hypercholesterolemia after long-term use (26 weeks) (Anderson, J. W. et al., Am. J. Clin. Nutr., (71): 1433–8 (2000)). Psyllium may offer an effective adjunct to diet therapy and provide an alternative to drugs in patients with mild hypercholesterolemia.

The data regarding the use of psyllium as a means of lowering blood glucose in type 2 diabetes are less convincing (Anderson, J. W. et al., Am. J. Clin. Nutr., (70): 466–73 (1999)). Fifty-six patients with type 2 diabetes and hypercholesterolemia were randomly assigned to consume 10.2 g of psyllium for 8 weeks or to a cellulose placebo along with a traditional diet for diabetes. The fibers were consumed 20 to 30 minutes before the morning and evening meals. Significant improvements were observed in serum lipids (both total cholesterol, p<0.05, and LDL-cholesterol, p<0.07) and these changes were similar to other studies (Anderson, J. W. et al., Am. J. Clin. Nutr., 71: 1433–8 (2000); Anderson, J. W. et al., Am. J. Clin. Nutr., (71): 472–9 (2000)). The all day glucose and postlunch glucose concentrations were 11% (p<0.05) and 19.2% (p<0.01) lower, respectively in the psyllium group. Thus, it appears that an efficacious dose of psyllium to lower blood lipids is the same as for lowering blood glucose.

In the nutritional supplements of the invention, a serving should provide from about 0.5 to about 5 g psyllium, with about 1 g of psyllium per serving (8 oz. water and 10–15 g dry mix) being particularly preferred. The daily allowance of psyllium should be from about 0.5 g to about 11 grams. The term "daily allowance" as defined herein should be understood as the amount of an ingredient, such as psyllium, provided to an individual in a single daily serving or as multiple daily servings, e.g., two daily servings. The addition of more psyllium beyond the ranges described herein will adversely affect the taste of the nutritional supplement and require the addition of calorie-containing nutrients to compensate. Further, higher use levels of psyllium also cause the liquid to gel after a few minutes, making it difficult to drink.

Fructose is a preferred carbohydrate for sweetening the nutritional supplement. It is sweeter than ordinary table sugar (sucrose), derived from beet or cane sugars, and has a low glycemic index (GI=32). Taken as part of a meal, fructose produces a smaller incremental rise in plasma glucose level does sucrose, glucose, potato starch, or wheat starch. From about 0.5 g to about 11 g fructose can be used; with about 2 g fructose per serving being perferred.

In preferred embodiments, it is desirable to incorporate barley (e.g., barley flakes) into the nutritional supplement as a carbohydrate and fiber source. Of all the grains, certain forms of barley have some of the lowest glycemic indexes. Pearled barley (GI=36) and cracked barley (GI=72) have lower glycemic indexes than sweet corn (GI=78), rolled barley (GI=94), and instant white rice (GI=128). Further, it is desirable to use barley with its bran still on it (referred to as "hulless barley"), so that the naturally occurring fiber remains. From about 0.5 g to about 11 g of barley per serving based upon a 10–15 g serving can be used; with about 1 g per serving being particularly preferred. Thus, it provides a low glycemic source of carbohydrate and a source of fiber (14%), both of which are advantageous in maintaining good glucose and weight control.

Konjac flour, which comes from a perennial tuber called Amorphophallus konjac, is a dietary fiber (90%) and a polysaccharide with a very high molecular weight. In addition, this glucomannan hydrocolloid has the ability to increase the viscosity of the intestinal fluid (digesta), thereby limiting the transport of glucose into the bloodstream (Vuksan, V. et al., submitted for publications, (2000)). Konjac mannan also has a low glycemic index, promoting weight loss by increasing satiety in obese and non-obese patients with type 2 diabetes (Doi, K. et al., *Progress in Obesity Research*, ch. 80: 507–14, (1990)). In preferred embodiments, the nutritional supplement should provide from about 0.5 g to about 11 g konjac per serving; with about 1 g of konjac mannan being preferred.

Protein

Sources of protein can be any suitable protein utilized in nutritional formulations and can include all high biological value proteins such as whey protein, whey protein concentrate, whey powder, egg, soy protein, soy protein isolate, caseinate (e.g., sodium caseinate, sodium calcium caseinate, calcium caseinate, potassium caseinate), animal and vegetable protein and mixtures thereof. When choosing a protein source, the biological value of the protein should be considered first, with the highest biological values being found in caseinate, whey, lactalbumin, soy, delactosed milk solids, egg albumin and whole egg proteins These proteins have high biological value; that is, they have a high proportion of the essential amino acids.

In a preferred embodiment, the protein is whey protein concentrate or other protein with a high biological value (e.g., casein, soy, milk, egg) comprising from about 1 to about 5 grams protein per serving. The preferred amount of protein is approximately 2 grams per serving.

In the case of lipodystrophy, the individual will need additional protein than required for type II diabetics and as such all high biological value proteins can be used in the formulation in amounts of from about 0.5 grams to about 25 grams protein, with from about 0.5 grams to about 5 grams protein being preferred, and about 1.5 grams being most preferred. Preferably the protein source is whey protein.

Chromium

Chromium in an essential trace element that participates in carbohydrate and lipid metabolism (Cataldo, C. B. et al., *Nutrition and Diet Therapy*, (N.Y.: West Publishing Company), pp. 205–6 (1995)). It is widespread in the diet and found in unrefined foods like liver, whole grains, nuts and cheeses. However, as the intake of refined foods increases, there is an increased chance of developing a deficiency. The Estimated Safe and Adequate Nutritional Intake for chromium is 50 to 200 $\mu$g per day. Most people are unable to achieve the minimum amount of chromium intake. Several studies have demonstrated that men take abut 33±3 $\mu$g and women take about 25±1 $\mu$g per day (Anderson, R. A. *Am. Coll. Nutr.*, (17): 548–55 (1998)).

One form, chromium picolinate, has been studied extensively for its effect on blood glucose management and weight loss. Chromium as picolinate appears to have a beneficial effect on fasting plasma glucose concentrations at doses between 200 and 1,000 $\mu$g daily. Most studies have shown the greatest benefit from at least 400 $\mu$g or more, and it seems to work whether it is given once or twice a day (Anderson, R. A., *Am. Coll. Nutr.*, (17): 548–55 (1998)). The proposed mechanism of action is that chromium increases the ability of insulin to bind to cells. It has been shown to maintain lean body mass during weight loss (Kaats, G. R. et al., *Curr. Ther. Res.*, 51: 261–74 (1992)). Chromium supplementation is not efficacious until it has been used for six weeks, and with long term use it continues to be effective.

Each serving of the nutritional supplement of the invention should provide the preferred range from about 50 to 1000 $\mu$g chromium per serving. The most preferred amount of chromium for the nutritional supplement is approximately 100 $\mu$g of chromium picolinate per serving, with two daily servings being preferred. Alternatively, chromium chloride may be used, but the picolinate form is preferred due to its beneficial effects on fasting plasma glucose (FPG) concentrations. Since the nutritional supplement is intended to supplement the diet of an individual, the daily allowance of chromium provided by the invention is intended to be less than the efficacious amount. The difference in the amount of chromium will likely be made up from the diet (e.g., nutritional supplements, foods, pharmaceutical compositions), which may comprise an additional 200 $\mu$g per day.

Ginseng

Ginseng (e.g., Panax ginseng) is a slow-growing perennial herb native to mountainous-forested areas in China, Korea, and parts of Russia. Its early therapeutic uses in Asian medicine included revitalization of energy, reduction of susceptibility to illness, and promotion of longevity. The active compounds are ginsenosides, and most commercially available products are standardized to a known concentration. More recently, ginseng was officially recognized by the German Pharmacopeia and approved in the Commission E monographs for use in geriatric remedies and tonics for invigoration and fortification.

Ginseng has also been shown to influence blood glucose concentrations (Sotaniemi, E. A. et al., *Diab. Care*, 18: 1373–75 (1995); Vuksan, V. et al., *Arch. Intern. Med.*, 160: 1009–13 (2000)). The Finns evaluated the effect of two doses of ginseng (100 mg and 200 mg) on glucose balance, serum lipids, and physical performance (Sotaniemi, E. A. et al., *Diab. Care*, 18: 1373–75 (1995)). Thirty-six newly diagnosed, non-insulin-dependent subjects with diabetes were randomized to one of the treatments or a placebo for 8 weeks. Both groups receiving the ginseng experienced a significant reduction in fasting plasma glucose ($p<0.05$). For the higher ginseng dose, but not the lower one, Hgb $Al_c$ was significantly reduced ($p<0.05$). In the two ginseng-treated groups, energy levels improved but serum lipids did not change.

In a more recent study, ginseng was administered to 9 subjects with type 2 diabetes in a large dose (3 g of Panax quinquefolius L) before or together with a glucose-containing solution, used for a glucose tolerance test (25 g oral glucose load) (Vuksan, V. et al., *Arch. Intern. Med.*, 160: 1009–13 (2000)). Compared to a placebo, ginseng significantly reduced the area under the curve (AUC) of glucose ($p<0.008$ over 120 minutes). The AUC was significantly lower ($p<0.05$) in the ginseng groups compared whether the ginseng was taken before (19±22%) or during (22±11%) the glucose administration.

The mechanism by which ginseng lowers blood glucose concentrations is unknown, although several have been proposed (Vuksan, V. et al., *Arch. Intern. Med.*, 160: 1009–13 (2000)). It has been proposed that ginseng slows the digestion of food, thereby decreasing the rate of carbohydrate absorption in the portal hepatic circulation. Ginseng has been shown to increase glucose transporter-2 protein in the liver of normal and hyperglycemic mice; glucose uptake also increases via the same transporter in sheep erythrocytes. Finally, ginseng may modulate insulin secretion. The action of the transporter-2 protein and insulin secretion appear to be modulated by nitric oxide, which may be stimulated by ginseng.

The nutritional supplement should contain from about 100 to 200 mg ginseng per serving in a concentrated form; less concentrated ginseng should be provided in amounts of from about 1 mg to about 5 g. Preferably, the nutritional supplement should provide approximately 100 mg of ginseng per serving. The amount is based on the treatment used in the Finnish study, whose conditions approximated usual care (i.e., showing the effect on FPG and Hgb $Al_c$ over a long period of time).

Sterols and Stanols

Phytosterols are naturally occurring constituents of plants. The most abundant is β-sitosterol, although others include campesterol and stigmasterol. Numerous reports exist in the medical literature describing the cholesterol-lowering effects of plant sterols and stanols (Jones, P. J. H. et al., *Metabolism*, 47: 751–6 (1998); Jones, P. J. H. et al., *Can. J. Physiol. Pharmacol.*, 75: 217–27 (1997); Halikainen, M. A. et al., *J. Nutr.*, 130: 767–76 (2000); Gylling, H. et al., *Circulation*, 96: 4226–31 (1997); Halikainen, M. A. et al., *Am. J. Clin. Nutr.*, 63: 403–10 (2000)). Although these compounds are normally consumed from plants, a typical diet only contains about 200 to 400 mg/day (Jones, P. J. H. et al., *Can. J. Physiol. Pharmacol.*, 75: 217–27 (1997)). A review of the literature supports the use of 1.6 to 3.0 g per day to achieve a significant reduction in total-and LDL-cholesterol levels. With these doses, total cholesterol has been shown to decrease 0.5 to 26% and LDL-cholesterol by 2 to 33%. The HDL-cholesterol is not affected by sterol ingestion.

A recent report showed that 1.6 g of a stanol ester for 4 weeks was sufficient to significantly decrease total cholesterol (6.8%; $p<0.001$) and LDL-cholesterol (5.6%; p 0.05) in hypercholesterolemic men and women (Halikainen, M. A. et al., *J. Nutr.*, 130: 767–76 (2000)). Increasing the dose to 2.4 or 3.2 g per day did not provide additional clinical benefit. When phytosterol levels are increased in the blood, nutritional cholesterol is inefficiently absorbed and cholesterol synthesis reduced. Both of these actions cause serum cholesterol levels to decrease (Jones, P. J. H. et al., *Can. J. Physiol. Pharmacol.*, 75: 217–27 (1997)).

The nutritional supplement should provide from about 0.5 to about 2 grams sterol, stanol or derivative of these, preferably a plant sterol or stanol. The sterol or stanol can be provided in the form of an ester and/or attached to a lecithin micelle. The supplement preferably provides 0.8 g of a plant (e.g., from soy, tall, with soy being preferred) sterol as a lecithin micelle in each serving so that use of the product twice a day will give the desired effect on blood lipids. It is recommended that each serving be taken with or at the completion of the two largest (e.g., lunch and dinner) meals so that the sterol can exert its maximum effect on the cholesterol-containing food. It has been reported that there is no therapeutic difference between plant stanol esters and plant sterol esters (Brief Critical Review, *Nutr.Rev.*, 56: 245–252 (1998)), so a plant stanol ester may alternatively be used.

In a particularly preferred embodiment, the sterol or stanol is incorporated into a micelle. The micelle can be produced using lecithin or other emulsifying agent. Known methods for producing lecithin micelles can be used. This should create at least the same cholesterol-lowering effect, if not more, because lecithin itself may reduce cholesterol levels (Knuiman, K. T. et al., *Am. J. Clin. Nutr.*, 49: 266–8 (1989); Polichetti et al., *Br. J. Nutr.*, 75: 471–8 (1996)). Nonetheless, sterol as a lecithin micelle should at least be as good as the ester form in a high-fat medium (e.g., margarine), the typical commercially available form, because a sterol-lecithin micelle has already been shown to be effective at reducing cholesterol absorption, thus theoretically lowering serum lipid levels in hypercholesterolemic patients (Ostlund, R. E. et al., *Am. J. Cl in. Nutr.*, 70: 826–31 (1999) and Ostlund, U.S. Pat. No. 5,932,562).

Other Cholesterol Lowering Agents

In addition to or alternative to the ingredients described above for cholesterol loweirng, other cholesterol-lowering agents may be used such as red yeast rice (about 1 to 20 grams; with about 1 to about 5 grams being preferred; and about 2.4 g/day of a 0.4% preparation being most preferred), oat or yeast β-glucan (about 1 to 20 grams; with about 1 to about 5 grams being preferred; and about 3 g/day being most preferred), or increasing the amount of psyllium (about 1 to 100 grams; with about 10 to about 50 grams being preferred; and about 10 to about 15 g/day being most preferred).

Lipid Source

Nutritional fish oil can be added to the nutritional supplement because it is a potent means of reducing serum triglycerides and is an anti-platelet aggregator (Gorlin, R., *Arch. Intern. Med.*, 148: 2043–8 (1988); Drevon, C. A., *Nutr. Rev.*, 50: 38–45(1992); Norum, K. R., *Nutr. Rev.*, 50: 30–37 (1992); Simopoulos, A. P., *Am. J. Clin. Nutr.*, 54: 438–63 (1991)). Patients with type 2 diabetes are often hypertriglyceridemic. Plasma triglyceride levels vary with the amount and type of fat in the diet (Norum, K. R., *Nutr. Rev.*, 50: 30–7 (1992)). Saturated fats increase triglycerides in the plasma whereas unsaturated (mono and poly) fats do not. A low-fat diet, rich in carbohydrates, also raises triglyceride levels.

The mechanism of action for lowering triglyceride levels is unknown, but the fish oil appears to slow the production of very low density lipoproteins produced in the liver through inhibition of apoprotein B synthesis (Gorlin, R., *Arch. Intern. Med.*, 148: 2043–8 (1988)). Hemodialyzed, hypertriglyceridemic patients consuming 2.5 to 3 g of omega-3 fatty acids experienced a 30% reduction in plasma triglycerides (Bonanome, A. et al., *Am. J. Clin. Nutr.*, 63: 261–6 (1996)). For changes in serum triglyceride levels to occur, more than 2 to 3 g of omega-3 fatty acids need to be ingested daily (Drevon, C. A., *Nutr. Rev.*, 50: 38–45 (1992)). Most commercial fish oil is 30% omega-3 fatty acids, so at least 6 g need to be consumed to meet this need. Continued consumption of the fish oil for years proves to be effective (Simopoulos, A. P., *Am.J. Clin. Nutr.*, 54: 438–63(1991)).

Fish oil also prolongs bleeding time, a measurement of platelet and vessel wall interaction (Gorlin, R., *Arch. Intern. Med.*, 148: 2043–8 (1988)). It is likely that platelet behavior is inhibited through the alteration of production of thromboxane $A_2$, when eicosapentanoic acid competes with arachidonic acid for space on the fatty acid chain of the phospholipids residing on the cell membrane. For changes to occur, at least 3.6 g of omega-3 fatty acids are needed for at least two weeks. (Gorlin, R., *Arch. Intern. Med.*, 148: 2043–8 (1988)). However, the combination of aspirin and fish oil increase bleeding time (an indication of less platelet aggregation) by more than the sum of the increases in bleeding time caused by aspirin or fish oil separately (Gorlin, R., *Arch. Intern. Med.*, 148: 2043–8 (1988)).

The nutritional supplement may contain a source of fat that provides from about 10% to about 80% omega-3 fatty acids in amounts of from about 0.5 g to about 5 g per serving. Examples of suitable fats included but are not limited to fish oil (e.g., from menhaden or sardines) and non-atherogenic oils such as vegetable oil (e.g., canola, olive, soy, safflower, sunflower, corn) and combinations thereof. In an embodiment, approximately 1 g of fish oil (30% omega-3 fatty acids) can be used, with two servings recommended per day. This dose alone will not achieve the desired biological effects of lowering triglyceride levels and reducing platelet aggregation, but it is assumed that the diet will supply the remaining omega-3 fatty acids and that the addition of a natural source of aspirin (described in detail below) will assure efficacy. In another preferred embodiment, the source of fat will be provided as a combination of fish oil and a non-atherogenic oil, such as a 1:1 mixture. In the most preferred emobodiment, only a non-atherogenic fat source is used, e.g., canola oil.

Salicylic Acid

Aspirin therapy is beneficial for patients with type 2 diabetes who are at risk of developing cardiovascular disease (American Diabetes Association, *Diab. Care*, (23): 1772–1773 (2000); Kajubi, S. K., Arch. Intern. Med., 160: 3945 (2000)). Patients should take one children's aspirin daily to supply 81 mg of acetylsalicylic acid. However, compliance with medications wanes as the number of drugs increase, and most people with diabetes are taking several. To overcome this phenomenon, willow bark (Salix alba) can be incorporated into the supplement of the invention, which contains a natural source of acetylsalicylic acid, the active compound known as aspirin. Thus, patients who consume the nutritional supplement twice daily will get sufficient willow bark to favorably modulate platelet function. Willow bark is officially recognized in the German Pharmacopeia and approved in the Commission E monographs for use as an analgesic.

In a preferred embodiment, the nutritional supplement can contain from about 20 to about 80 mg salicylic acid source. For example, a dose of 4 to 8 g willow bark in the form of dried bark, tincture, dry extract, etc. is equivalent to 40 to 80 mg of total salicin. The dose of willow bark should be added in amounts that supply 40 mg of the active compound, actetylsalicylic acid, per serving. Aspirin can also be used, particularly for pharmaceutical compositions.

Glutamine

Glutamnine has been shown to benefit bowel and immune function in these patients (Shabert J., Ehrlich N., *The Ultimate Nutrient Glutamine*, Garden city Park, N.Y.; Avery Publishing Group, 1994). In one embodiment, the nutritional supplement can contain from about 1 gram to about 80 grams of glutamine. In another embodiment, the amount of glutamine can be from about 20 grams to about 40 grams, with about 40 grams being most preferred.

Further Ingredients

The nutritional supplement can also contain other ingredients such as one or a combination of other vitamins, minerals, antioxidants, herbs (e.g., ginkgo biloba), fiber and other nutritional supplements. Selection of one or several of these ingredients is a matter of formulation design, consumer and end-user preference. The amount of these ingredients added to the nutritional supplements of this invention are readily known to the skilled artisan and guidance to such amounts can be provided by the RDA and DRI (Dietary Reference Intake) doses for children and adults. Vitamins and minerals that can be added include, but are not limited to, calcium phosphate or acetate, tribasic; potassium phosphate, dibasic; magnesium sulfate or oxide; salt (sodium chloride); potassium chloride or acetate; ascorbic acid; ferric orthophosphate; niacin amide; zinc sulfate or oxide; calcium pantothenate; copper gluconate; riboflavin; beta-carotene; pyridoxine hydrochloride; thiamin mononitrate; folic acid; biotin; chromium chloride or picolinate; potassium iodide; selenium; sodium selenate; sodium molybdate; phylloquinone; Vitamin $D_3$; cyanocobalamin; sodium selenite; copper sulfate; Vitamin A; Vitamin E; vitamin $B_6$ and hydrochloride thereof; Vitamin C; inositol; Vitamin $B_{12}$; potassium iodide.

The amount of other additives per unit serving are a matter of design and will depend upon the total number of unit servings of the nutritional supplement daily administered to the patient. The total amount of other ingredients will also depend, in part, upon the condition of the patient. Preferably the amount of other ingredients will be a fraction or multiplier of the RDA or DRI amounts. For example, the nutritional supplement will comprise 50% RDI (Reference Daily Intake) of vitamins and minerals per unit dosage and the patient will consume two units per day.

Flavors, coloring agents, spices, nuts and the like can be incorporated into the product. Flavorings can be in the form of flavored extracts, volatile oils, chocolate flavorings (e.g., non-caffeinated cocoa or chocolate, chocolate substitutes such as carob), peanut butter flavoring, cookie crumbs, crisp rice, vanilla or any commercially available flavoring. Flavorings can be protected with mixed tocopherols. Examples of useful flavorings include but are not limited to pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, cherry oil, walnut oil, cinnamon oil, clove oil, or peppermint oil; peanut butter, chocolate flavoring, vanilla cookie crumb, butterscotch or toffee. In a preferred embodiment, the nutritional supplement contains berry or other fruit flavor. The food compositions may further be coated, for example with a yogurt coating if it is as a bar.

Emulsifiers may be added for stability of the final product. Examples of suitable emulsifiers include, but are not limited to, lecithin (e.g., from egg or soy), and/or mono-and di-glycerides. Other emulsifiers are readily apparent to the skilled artisan and selection of suitable emulsifier(s) will depend, in part, upon the formulation and final product.

Preservatives may also be added to the nutritional supplement to extend product shelf life. Preferably, preservatives such as potassium sorbate, sodium sorbate, potassium benzoate, sodium benzoate or calcium disodium EDTA are used.

In addition to the carbohydrates described above, the nutritional supplement can contain artificial sweeteners, e.g., saccharides, cyclamates, aspartamine, aspartame, acesulfame K, and/or sorbitol. Such artificial sweeteners can be desirable if the nutritional supplement is intended for an overweight or obese individual, or an individual with type II diabetes who is prone to hyperglycemia.

Manufacture of the Nutritional Supplement

The nutritional supplements of the present invention may be formulated using any pharmaceutically acceptable forms of the vitamins, minerals and other nutrients discussed above, including their salts. They may be formulated into capsules, tablets, powders, suspensions, gels or liquids optionally comprising a physiologically acceptable carrier, such as but not limited to water, milk, juice, soda, starch, vegetable oils, salt solutions, hydroxymethyl cellulose, carbohydrate. In a preferred embodiment, the nutritional supplements may be formulated as powders, for example, for mixing with consumable liquids, such as milk, juice, sodas, water or consumable gels or syrups for mixing into other nutritional liquids or foods. The nutritional supplements of this invention may be formulated with other foods or liquids to provide premeasured supplemental foods, such as single serving beverages or bars, for example.

In a particularly preferred embodiment, the nutritional supplement will be formulated into a nutritional beverage, a form which has consumer appeal, is easy to administer and incorporate into one's daily regimen, thus increasing the chances of patient compliance. To manufacture the beverage, the ingredients are dried and made readily soluble in water.

To manufacture such a food bar, the dry ingredients are added with the liquid ingredients in a mixer and mixed until the dough phase is reached; the dough is put into an extruder and extruded; the extruded dough is cut into appropriate lengths; and the product is cooled.

For manufacture of other foods or beverages, the ingredients comprising the nutritional supplement of this invention can be added to traditional formulations or they can be used to replace traditional ingredients. Those skilled in food formulating will be able to design appropriate foods/beverages with the objective of this invention in mind.

The nutritional supplement can be made in a variety of forms, such as puddings, confections, (i.e., candy), nutritional beverages, ice cream, frozen confections and novelties, or non-baked, extruded food products such as bars. The preferred form is a powder to add to a beverage or a non-baked extruded nutritional bar.

In another embodiment, the ingredients can be separately assembled. For example, certain of the ingredients (e.g., the bitter tasting ones) can be assembled into a tablet or capsule using known techniques for their manufacture. The remaining ingredients can be assembled into a powder or nutritional bar, as described herein. The two assembled forms comprise the nutritional supplement and can be packaged together or separately, such as in the form of a kit, as described below. Further, they can be administered together or separately, as desired.

Use of the Nutritional Supplement

The ingredients described above aid in the management of blood glucose levels, blood lipid levels, and platelet aggregation. The importance of managing blood glucose levels through foods and regulation of insulin contribute to the management of hyperglycemia and overweight, both seen in type 2 diabetics (Slabber, M. et al., *Am. J. Clin. Nutr.*, 60: 48–53 (1994)). In addition, patients with type 2 diabetes typically have abnormally high total- and LDL-cholesterol, low high density lipoprotein (HDL) cholesterol, and are hypertriglyceridemnic—conditions that give diabetics a two to fourfold excess risk of coronary heart disease. Diabetics also suffer from abnormal platelet function, specifically, platelet aggregation, which leads to atherosclerosis and vascular thrombosis, precursors of cardiovascular disease and premature death (American Diabetes Association, *Diab. Care*, (23): 1772–1773 (2000)). Early incorporation of the food ingredients contained in the preferred embodiment of the invention may delay the need for lipid-lowering and anti-platelet-aggregating drugs.

The nutritional supplement can provide benefits to HIV-infected individuals with lipodystrophy. The metabolic changes associated with lipodystrophy can be minimized, reduced and/or prevented by administration of the nutritional supplement of this invention. The metabolic changes are similar to those seen in diabetics, namely insulin resistance, abnormal lipid and trygliceride levels, glucose intolerance accelerated atherosclerosis and enhanced cardiovascular risks. Thus, the benefits of the invention to diabetics can be applicable to individuals with lipodystrophy. Further, control of these metabolic changes may reduce, minimize or prevent the body composition changes (e.g., fat accumulation, fat redistribution) typically associated with lipodystrophy. HIV-infected individuals on antiretroviral therapy (HAART), particularly those receiving protease inhibitors, should benefit from the nutritional supplement as these therapies are thought to be a cause of lipodystrophy. Diet and exercise coupled with the use of the nutritional supplement of the invention should provide a therapeutic regimen to reduce the risks associated with lipodystrophy.

The composition and nutritional supplements of the invention are intended to be orally administered daily. Based on the serving size of 10–15 g powder in 8 oz. water, the recommended dosage is twice daily. For example, if the supplement is in the form of a beverage or food bar, then the patient would consume one after or during each of the two largest meals, where the greatest amounts of fats and cholesterol are likely to be consumed. The recommended daily amounts of each ingredient, as described above, serve as a guideline for formulating the nutritional supplements of this invention. The actual amount of each ingredient per unit dosage will depend upon the number of units daily administered to the individual in need thereof. This is a matter of product design and is well within the skill of the nutritional supplement formulator.

The ingredients can be administered in a single formulation or they can be separately administered. For example, it may be desirable to administer the bitter tasting ingredients in a form that masks their taste (e.g., capsule or pill form) rather than incorporating them into the nutritional composition itself (e.g., powder or bar). Thus, the invention also provides a pharmaceutical pack or kit comprising one or more containers filled with one or more of the ingredients of the nutritional compositions of the invention (e.g., nutritional supplement in the form of a powder and capsules containing herbs and aspirin). Optionally associated with such container(s) can be a notice in the form prescribed by a government agency regulating the manufacture, use or sale of pharmaceutical products, which notice reflects approval by the agency of manufacture, use of sale for human administration. The pack or kit can be labeled with information regarding mode of administration, sequence of administration (e.g., separately, sequentially or concurrently), or the like. The pack or kit may also include means for reminding the patient to take the therapy. The pack or kit can be a single unit dosage of the combination therapy or it can be a plurality of unit dosages. In particular, the agents can be separated, mixed together in any combination, present in a formulation or tablet. Agents assembled in a blister pack or other dispensing means is preferred.

All references provided cited are incorporated by reference in their entirety.

EXAMPLE

Recipe for a Nutritional Supplement for Patients with Type 2 Diabetes Mellitus In one embodiment, the nutritional supplement is a beverage that provides 45 kcal/unit serving, where one unit serving is a 11 gram powder in 8 oz. of water, and is to be administered twice daily. The invention has the following characteristics:

- approximately 7 g carbohydrate: fructose (2 g), konjac flour (1 g) (from Opta Food Ingredients, Bedford, Mass.), psyllium (1 g), 2 g other sources (e.g., whey, lecithin, willow bark, flavors, colors) barley (1 g); aspartame to sweeten;
- approximately 2 g protein: preferably, whey protein concentrate. Soy, casein, or other high biological value proteins may be substituted to improve flavor;
- approximately 1.5 g fat: as 1 g canola oil and 0.5 g other (e.g., lecithin, whey);
- approximately 1.6 g plant component: mixture of lecithin and of plant sterol (lowers total and LDL-C) as a lecithin micelle;
- approximately 100 μg chromium: as picolinate (from AMBI/Nutrition 21);
- approximately 267 mg willow bark: (Net Chem, Seattle, Wash., 15% concentrate or active compound); and
- approximately 100 mg ginseng (Gerimax, Ginseng Extract, (GGE) Dansk Droge A/S, Denmark).

While this invention has been particularly shown and described with references to preferred embodiments thereof, it will be understood by those skilled in the art that various changes in form and details may be made therein without departing from the scope of the invention encompassed by the appended claims.

What is claimed is:

1. A nutritional supplement, comprising a low-glycemic index carbohydrate source, a source of protein, a source of fat, a source of sterol and/or stanol, a source of chromium, a source of salicylic acid, and a source of ginseng.

2. The nutritional supplement of claim 1, wherein the nutritional supplement is in the form of a powder.

3. The nutritional supplement of claim 1, wherein the nutritional supplement is in the form of an extruded bar.

4. The nutritional supplement of claim 1, wherein the carbohydrate source further provides a source of fiber.

5. The nutritional supplement of claim 3, wherein the carbohydrate source comprises barley flakes, konjac mannan, fructose or combination thereof.

6. The nutritional supplement of claim 4, wherein the carbohydrate source is psyllium.

7. The nutritional supplement of claim 1, wherein the protein source is of a high biological value.

8. The nutritional supplement of claim 6, wherein the protein source comprises at least one protein source selected from the group consisting of whey, casein, soy, milk, egg and combination thereof.

9. The nutritional supplement of claim 1, wherein the fat source is a nonatherogenic oil.

10. The nutritional supplement of claim 9, wherein the nonatherogenic oil is a vegetable oil.

11. The nutritional supplement of claim 1, wherein the fat source is a fish oil.

12. The nutritional supplement of claim 1, wherein the fat source is a combination of fish oil and a nonatherogenic oil.

13. The nutritional supplement of claim 12, wherein the fish oil is from menhaden or sardines and the nonatherogenic oil is a vegetable oil.

14. The nutritional supplement of claim 10, wherein the vegetable oil comprises at least one vegetable oil selected from the group consisting of canola, olive, soy, safflower, sunflower, corn and combination thereof.

15. The nutritional supplement of claim 1, wherein the source of sterol or stanol is a plant.

16. The nutritional supplement of claim 15, wherein the sterol and/or stanol is contained in a lecithin micelle.

17. The nutritional supplement of claim 1, wherein the sterol and/or stanol is in the form of an ester.

18. The nutritional supplement of claim 17, wherein the sterol and/or stanol ester is contained in a lecithin micelle.

19. The nutritional supplement of claim 1, wherein the source of chromium is in the picolinate form.

20. The nutritional supplement of claim 1, wherein the source of chromium is in the chloride form.

21. The nutritional supplement of claim 1, wherein the source of salicylic acid is from willow bark.

22. The nutritional supplement of claim 1, wherein the source of salicylic acid is acetylsalicylic acid.

23. The nutritional supplement of claim 1, wherein the ingredients are separately assembled.

24. The nutritional supplement of claim 1, further comprising from about 1 to about 80 grams glutamine; from about 100 mg to about 20 grams source of N-acetylcysteine, and from about 0.5 to about 25 grams whey protein.

25. A nutritional supplement comprising, about 10 to about 15 g powder comprising from about 1 to about 25 grams carbohydrate, from about 0.5 to about 11 grams psyllium, konjac mannan, fructose and barley; from about 1 to about 10 grams protein, from about 1 to about 10 grams fat, from about 0.5 to about 4 grams plant sterol, from about 1 to about 2000 micrograms chromium, from about 1 to about 325 milligrams salicylic acid, and from about 1 mg to about 5 grams ginseng.

26. A nutritional supplement comprising, about 10 to about 15 g powder conmprising from about 2 to about 10 grams carbohydrate, from about 1 to about 5 grams protein, from about 1 to about 5 grams fat, from about 0.5 to about 2.0 grams plant sterol, from about 50 to about 1000 micrograms chromium, from about 20 to about 80 milligrams salicylic acid, and from about 100 mg to about 200 grams ginseng.

27. The nutritional supplement of claim 26, wherein the carbohydrate comprises from about 0.5 to about 5 grams psyllium, konjac mannan, fructose, barley flakes or combinations thereof.

28. The nutritional supplement of claim 26, wherein the fat contains omega-3 fatty acids.

29. The nutritional supplement of claim 28, wherein the fat is comprised of 10% to about 80% omega-3 fatty acids.

30. A food or beverage comprising the nutritional supplement of claim 1.

31. A pharmaceutical composition comprising the nutritional supplement of claim 1.

32. A method of providing an individual with nutritional supplementation that aids in the management of blood glucose levels, comprising administering to an individual in need thereof the nutritional supplement of claim 1, in an amount sufficient to manage blood glucose levels.

33. A method of providing an individual with nutritional supplementation that aids in the management of blood lipid levels, comprising administering to an individual in need thereof the nutritional supplement of claim 1, in an amount sufficient to manage blood lipid levels.

34. A method of decreasing the risk of developing microvascular complications associated with type 2 diabetes or lipodystrophy, comprising the administration of the supplement of claim 1, in an amount sufficient to decrease the risk of developing microvascular complications.

35. A method of decreasing the risk of developing macrovascular complications associated with type 2 diabetes or lipodystrophy, comprising the administration of the supplement of claim 1, in an amount sufficient to decrease the risk of developing macrovascular complications.

36. A method for managing platelet adherence, comprising administering to an individual in need thereof the nutritional supplement of claim 1.

37. A kit comprising:
  a) one or more ingredients comprising the nutritional supplement of claim 1 provided in a capsule or tablet; and
  b) the remaining ingredients of the nutritional supplement provided as a powder or nutritional bar.

38. A nutritional supplement comprising from about 1 to about 25 grams carbohydrate, including from about 0.5 to about 11 grams psyllium, from about 0.5 to about 11 grams konjac mannan, from about 0.5 to about 11 grams fructose and from about 0.5 to about 11 grams barley; from about 1 to about 10 grams protein, from about 1 to about 10 grams fat, from about 0.5 to about 4 grams plant sterol, from about 1 to about 2000 micrograms chromium, from about 1 to about 325 milligrams salicylic acid, and from about 1 mg to about 5 grams ginseng.

39. A nutritional supplement comprising from about 2 to about 10 grams carbohydrate, from about 1 to about 5 grams protein, from about 1 to about 5 grams fat, from about 0.5 to about 2.0 grams plant sterol, from about 50 to about 1000 micrograms chromium, from about 20 to about 80 milligrams salicylic acid, and from about 100 mg to about 200 grams ginseng.

40. The nutritional supplement of claim 39, wherein the carbohydrate comprises from about 0.5 to about 5 grams psyllium, konjac mannan, fructose, barley flakes or combinations thereof.

41. The nutritional supplement of claim 39, wherein the fat contains omega-3 fatty acids.

42. The nutritional supplement of claim 41, wherein the fat is comprised of 10% to about 80% omega-3 fatty acids.

* * * * *